US007232571B2

(12) United States Patent
Farmer et al.

(10) Patent No.: US 7,232,571 B2
(45) Date of Patent: *Jun. 19, 2007

(54) **METHODS FOR REDUCING CHOLESTEROL USING *BACILLUS COAGULANS* SPORES, SYSTEMS AND COMPOSITIONS**

(75) Inventors: Sean Farmer, La Jolla, CA (US); Andrew R. Lefkowitz, Cleveland, OH (US)

(73) Assignee: Ganeden Biotech, Inc., Mayfield Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/978,726

(22) Filed: Nov. 1, 2004

(65) Prior Publication Data

US 2006/0093591 A1    May 4, 2006

Related U.S. Application Data

(63) Continuation of application No. 09/647,695, filed on Apr. 6, 2001, now Pat. No. 6,811,786, which is a continuation of application No. PCT/US99/07360, filed on Apr. 1, 1999.

(51) Int. Cl.
*A61K 33/00* (2006.01)
*A61K 33/24* (2006.01)
*A61K 39/07* (2006.01)
*C12N 1/20* (2006.01)

(52) U.S. Cl. .............................. 424/247.1; 424/93.46; 424/600; 424/617; 435/252.5

(58) Field of Classification Search ............. 424/247.1, 424/93.46, 600, 617; 435/252.5
See application file for complete search history.

(56) References Cited

U.S. PATENT DOCUMENTS

| | | | |
|---|---|---|---|
| 4,110,477 A | 8/1978 | Naruse et al. | 426/46 |
| 4,323,651 A | 4/1982 | Long et al. | 435/207 |
| 4,980,180 A | 12/1990 | Cully et al. | 426/47 |
| 5,079,164 A | 1/1992 | Kirkovits et al. | 435/252.5 |
| 5,102,800 A | 4/1992 | Hirikoshi et al. | 435/193 |
| 5,176,911 A | 1/1993 | Tosi et al. | 424/93 |
| 5,200,336 A | 4/1993 | Kong et al. | 435/199 |
| 5,427,777 A | 6/1995 | St. Pierre et al. | 424/78.01 |
| 5,531,989 A | 7/1996 | Paul | 424/93.4 |
| 5,607,669 A | 3/1997 | Mandeville, III et al. | 424/78.12 |
| 6,811,786 B1 * | 11/2004 | Farmer et al. | 424/247.1 |
| 2001/0006644 A1 | 7/2001 | Bova et al. | 424/400 |

FOREIGN PATENT DOCUMENTS

| | | |
|---|---|---|
| EP | 0307158 | 3/1989 |
| EP | 0457539 | 11/1991 |
| JP | 62061572 | 3/1987 |
| WO | WO 93/14187 | 7/1993 |
| WO | WO 94/11492 | 5/1994 |

OTHER PUBLICATIONS

Baker et al., "Growth Requirements of 94 Strains of *Thermophilic bacilli*," CA. J. Microbiol., 6:557-563, 1960.
Bergey's Manual of Systemic Bacteriology, vol. 2, Sneath, P.H.A. et al., eds., Williams & Wilkens, Baltimore, MD, 1986.
Elmer et al., "A Neglected Modality for the Treatment and Prevention of Selected Intestinal and Vaginal Infections," JAMA, 275: 870-876, 1996.
Gorbach, "Lactic Acid Bacteria and Human Health," Ann. Med., 22:37-41, 1990.
Lidbeck et al., "*Lactobacilli*, anticarcinogenic activities and human intestinal microflora," Eur. J. Cancer Prev. 1:341-353, 1992.
Malin et al., "Promotion of IgA Immune Response in Patients with Crohn's Disease by Oral Bacteriotherapy with *Lactobacillus* GG," Ann. Nutr. Metab., 40:137-145,1996.
Mohan et al., "Preliminary Observations on Effect of *Lactobacillus sporogenes* on Serum Lipid Levels in Hypercholesterolemin Patients," The Indian Journal of Medical Research, 92; 431-432, 1990.
Molin et al., "Effect of Fermented Oatmeal Soup on te Cholesterol Level and *Lactobacillus* Colonization of Rat Intestinal Mucosa," Antonie Van Leeuwenhoek, 61(3); 167-173, 1992.
Mitsuoka et al., "Effects of *Fructo-oligosaccharides* on Blood Glucose and Serum Lipids in Diabetic Subjects," Nutrition Research, 4:961-966, 1984.
Nakamura et al., "Taxonomic Study of *Bacillus coagulans* Hammer 1915 with a Proposal for *Bacillus smithii* sp. nov.," Int. J. Syst. Bacteriol., 38:63-73, 1988.
Perdigon et al., "Symposium: Probiotic Bacteria for Humans: Clinical Systems for Evaluation of Effectiveness," J. Dairy Sci., 78:1597-1606,1995.
Rafter et al., "The Role of Lactic Acid Bacteria in Colon Cancer Prevention," Scand. J. Gastroenterol., 80:497-502, 1995.
Reid et al., "Is there a Role for *Lactobacilli* in Prevention of Urogenital and Intestinal Infections?" Clin. Microbiol. Rev., 335-344, 1990.
Salimen et al., "Clinical uses of probiotics for stabilizing the gut mucosal barrier: successful strains and future challenges," Antonie Van Leeuwenhoek, 70(2-4): 347-358, 1996.
Schaafsma et al., "Effects of a Milk Product, Fermented by *Lactobacillus acidophilus* and With *Fructo-ogliosaccharides* Added, on Blood Lipids in Male Vlounteers," European Journal of Clinical Nutrition, 52(6); 436-440, 1998.
Winberg et al., "Pathogenesis of urinary tract infection- experimental studies of vaginal resistance to colonization," Pediatr. Nephrol., 7:509-514, 1993.
Fukushima et al., "The effect of a probiotic on faecal and liver lipid classes in rats", Br. J. Nutr., 73(5):701-710 (1995).

* cited by examiner

*Primary Examiner*—Ruth A Davis
(74) *Attorney, Agent, or Firm*—Mintz, Levin, Cohn, Ferris, Glovsky and Popeo, P.C.; Ingrid A. Beattie

(57) ABSTRACT

The invention describes therapeutic compositions including a lactic acid-producing bacteria, such as isolated *Bacillus coagulans*, in combination with a bifidogenic oligosaccharides or other cholesterol-reducing agents for use in reducing LDL cholesterol and serum triglycerides. Also described are therapeutic methods using the compositions and systems containing the therapeutic compositions.

27 Claims, No Drawings

METHODS FOR REDUCING CHOLESTEROL USING *BACILLUS COAGULANS* SPORES, SYSTEMS AND COMPOSITIONS

RELATED APPLICATIONS

This application is a continuation application of U.S. Pat. No. 09/647,695, filed Apr. 6, 2001, now U.S. Pat. No. 6,811,786, which is a continuation application of PCT/US99/07360, filed Apr. 1, 1999, each of which are incorporated by reference in its entirety.

TECHNICAL FIELD

This invention relates to utilizing a probiotic organism in a therapeutic composition, and specifically relates to the use of a lactic acid-producing bacteria, preferably *Bacillus coagulans* spores, for control and reduction of serum cholesterol.

BACKGROUND OF THE INVENTION

Probiotic agents are organisms that confer a benefit when they grow in a particular environment, often by inhibiting the growth of other biological organisms in the same environment. Examples of probiotics include bacteria and bacteriophages which can grow in the intestine, at least temporarily, to displace or destroy pathogens and provide other benefits to the host organism (Salminen et al, *Antonie Van Leeuwenhoek*, 70 (2–4): 347–358, 1996; Elmer et al, JAMA, 275:870–876, 1996; Rafter, *Scand. J. Gastroenterol.* 30:497–502, 1995; Perdigon et al, *J. Dairy Sci.*, 78:1597–1606, 1995; Gandi, *Townsend Lett. Doctors & Patients*, pp. 108–110, January 1994; Lidbeck et al, *Eur. J. Cancer Prev.* 1:341–353, 1992).

The therapeutic use of probiotic bacteria, especially *Lactobacillus* strains, that colonize the gut has been previously disclosed (Winberg et al, *Pediatr. Nephrol.* 7:509–514, 1993; Malin et al, *Ann. Nutr. Metab.* 40:137–145, 1996; and U.S. Pat. No. 5,176,911).

Lactic acid producing bacteria (e.g., *Bacillus, Lactobacillus* and *Streptococcus* species) have been used as food additives and there have been some claims that they provide nutritional and therapeutic value (Gorbach, *Ann. Med.* 22:37–41, 1990; Reid et al, *Clin. Microbiol. Rev.*, 3:335–344, 1990).

*Bacillus coagulans* is a non-pathogenic gram positive spore-forming bacteria that produces L(+) lactic acid (dextrorotatory) in homofermentation conditions. It has been isolated from natural sources, such as heat-treated soil samples inoculated into nutrient medium (*Bergey's Manual of Systemic Bacteriology*, Vol. 2, Sneath, P. H. A. et al., eds., Williams & Wilkins, Baltimore, Md., 1986). Purified *B. coagulans* strains have served as a source of enzymes including endonucleases (e.g., U.S. Pat. No. 5,200,336), amylase (U.S. Pat. No. 4,980,180), lactase (U.S. Pat. No. 4,323,651) and cyclo-malto-dextrin glucano-transferase (U.S. Pat. No. 5,102,800). *B. coagulans* has been used to produce lactic acid (U.S. Pat. No. 5,079,164). A strain of *B. coagulans* (referred to as *L. sporogenes* Sakaguti & Nakayama (ATCC 31284)) has been combined with other lactic acid producing bacteria and *B. natto* to produce a fermented food product from steamed soybeans (U.S. Pat. No. 4,110,477). *B. coagulans* strains have also been used as animal feeds additives for poultry and livestock to reduce disease and improve feed utilization and, therefore, to increase growth rate in the animals (International PCT Pat. Applications No. WO 9314187 and No. WO 9411492).

In particular, *B. coagulans* strains have been used to reduce serum cholesterol in certain formulations (Mohan et al, *Indian J. Medical Research*, 92:431–432, 1990), although this approach did not reduce triglycerides sufficiently and resulted in excessive reductions on "good" cholesterol, e.g., high density lipoprotein (HDL).

Supplementation of diet with fructo-oligosaccharides (FOS) have been reported to provide health benefits including reduction of serum triglycerides. Mitsuoka et al, *Nutrition Research*, 4:961–966, 1984.

However, there remains a need for control of cholesterol to treat cholesterol related diseases.

SUMMARY OF THE INVENTION

It has now been discovered that serum cholesterol can be controlled and reduced while maintaining or increasing HDL by use of a combination of active agents in a therapeutic composition that includes a non-pathogenic lactic acid producing bacteria, such as *Bacillus coagulans*, and a therapeutic agent selected from the group consisting of an effective amount of a cholesterol-reducing agent and a bifidogenic oligosaccharide.

According to a preferred embodiment of the invention, there is provided a composition comprising an isolated *Bacillus coagulans* strain in combination with an effective amount of a fructo-oligosaccharide (FOS) in a pharmaceutically acceptable carrier suitable for administration to the digestive track of a human. In one embodiment of the composition, the *Bacillus coagulans* strain is included in the composition in the form of spores. In another embodiment, the *Bacillus coagulans* strain is included in the composition in the form of a dried cell mass.

The invention also describes a method for decreasing serum cholesterol and increasing serum HDL in a patient comprising administering an effective amount of a composition comprising viable lactic acid-producing bacteria and a therapeutic agent selected from the group consisting of an effective amount of a cholesterol-reducing agent and a bifidogenic oligosaccharide. The composition may optionally include a cholic acid complexation agent such as a metal salt and the like.

The invention also describes a therapeutic system for reducing serum cholesterol comprising a container comprising a label and a composition as described herein, wherein said label comprises instructions for use of the composition for reduction of serum cholesterol.

It should be understood that both the foregoing general description and the following detailed description are exemplary and explanatory only and are not restrictive of the invention as claimed.

DETAILED DESCRIPTION OF THE INVENTION

The present invention is directed to the discovery that non-pathogenic lactic acid-producing bacteria (i.e., "probiotic bacteria"), such as the exemplary *Bacillus coagulans*, can be used in therapeutic compositions as a probiotic in combination with a bifidogenic oligosaccharide or other functional hyperlipidemia drugs and supplements for reducing and/or controlling cholesterol in humans. The invention therefore describes various therapeutic compositions, methods for using the compositions and systems containing the therapeutic compositions.

A. Probiotic Lactic Acid-Producing Bacteria

A probiotic bacteria suitable for use in the methods and compositions of the invention as defined for use in the present invention produces lactic acid and is non-pathogenic. There are many suitable bacteria identified as described herein, although the invention is not limited to currently known bacterial species insofar as the purposes and objectives of the bacteria is described. The property of lactic acid production is key to the effectiveness of the probiotic lactic acid-producing bacteria of this invention because the lactic acid production increases acidity in the local micro floral environment, which does not support growth of many deleterious and undesirable bacteria and fungi. By the mechanism of lactic acid production, the probiotic inhibits growth of competing and deleterious bacteria.

As used herein, "probiotic" refers to microorganisms that form at least a part of the transient or endogenous flora and thereby exhibit a beneficial prophylactic and/or therapeutic effect on the host organism. Probiotics are generally known to be safe by those skilled in the art (i.e., non-pathogenic). Although not wishing to be bound by any particular mechanism, the prophylactic and/or therapeutic effect of a lactic acid-producing bacteria of this invention results in part from competitive inhibition of growth of pathogens due to superior colonization, parasitism of undesirable microorganisms, lactic acid production and/or other extracellular products having antimicrobial activity, or combinations thereof. These products and activities of a lactic acid-producing bacteria of this invention act synergistically to produce the beneficial probiotic effect.

Typical lactic acid-producing bacteria (i.e., a "lactic acid bacteria") useful as a probiotic of this invention are efficient lactic acid producers which include non-pathogenic members of the *Bacillus* genus which produce hydrolases or other enzymes which deconjugate bile salts to liberate cholesterol in the form of free cholic acid, all members of the *Lactobacillus* and *Sporolactobacillus* genus and all members of the *Bifidobacterium* genus, although certain species are particularly preferred as described herein.

Exemplary lactic acid-producing non-pathogenic *Bacillus* species are *Bacillus coagulans, Bacillus coagulans* Hammer and *Bacillus brevis* subspecies coagulans.

Exemplary lactic acid-producing *Lactobacillus* species include *Lactobacillus acidophilus, Lactobacillus casei, Lactobacillus* DDS-1, *Lactobacillus* GG, *Lactobacillus rhamnosus, Lactobacillus plantarum, Lactobacillus salivarius* and *Lactobacillus sporogenes* (aka *B. coagulans*).

Exemplary lactic acid-producing *Sporolactobacillus* species include all *Sporolactobacillus* species, including *Sporolactobacillus* P44.

Exemplary lactic acid-producing *Bifidobacterium* species include *Bifidobacterium adolescentis, Bifidobacterium animalis, Bifidobacterium bifidum, Bifidobacterium bifidus, Bifidobacterium breve, Bifidobacterium infantis, Bifidobacterium infantus* and *Bifidobacterium longum*.

There are several *Bacillus* species particularly useful according to the present invention, including the lactic acid-producers *Bacillus coagulans* and *Bacillus laevolacticus*. Although exemplary of the invention, *Bacillus coagulans* is only a model for the other acid producing species of probiotic bacteria useful in the invention, and therefore the invention is not to be considered as limiting and it is intended that any of the acid producing species of probiotic bacteria can be used in the compositions, therapeutic systems and methods of the present invention.

There are a variety of different *Bacillus* species useful in the present invention, including, but not limited to many different strains available through commercial and public sources, such as the American Type Culture Collection (ATCC). For example, *Bacillus coagulans* strains are available as ATCC Accession Numbers 15949, 8038, 35670, 11369, 23498, 51232, 11014, 31284, 12245, 10545 and 7050. *Bacillus laevolacticus* strains are available as ATCC Accession Numbers 23495, 23493, 23494, 23549 and 23492.

A *Bacillus* species is particularly suited for the present invention, particularly species having the ability to form spores which are relatively resistant to heat and other conditions, making them ideal for storage (shelf-life) in product formulations, and ideal for survival and colonization of tissues under conditions of pH, salinity, and the like in tissues of the gut. Additional useful properties include being non-pathogenic, aerobic, facultative and heterotrophic, rendering these species safe, and able to colonize the gut.

Because *Bacillus* spores are heat-resistant and additionally can be stored as a dry power, they are particularly useful for formulation into and manufacture of therapeutic formulations in the form of dry products.

Exemplary methods and compositions are described herein using *Bacillus coagulans* as a probiotic.

Purified *Bacillus coagulans* is particularly useful as a probiotic in the present invention. Probiotic *B. coagulans* is non-pathogenic. The Gram positive rods of *B. coagulans* have a cell diameter of greater than 1.0 micrometer ($\mu$m) with variable swelling of the sporangium, without parasporal crystal production.

Because *B. coagulans* forms heat-resistant spores, it is particularly useful for making pharmaceutical compositions that require heat and pressure in their manufacture. Formulations that include viable *B. coagulans* spores in a pharmaceutically acceptable carrier are particularly preferred for making and using compositions according to the present invention.

The growth of these various *Bacillus* species to form cell cultures, cell pastes and spore preparations is generally well known in the art. Exemplary culture and preparative methods are described herein for *Bacillus coagulans* and can readily be used and/or modified for growth of the other lactic acid producing bacteria of this invention.

1. Sources of *B. coagulans*

Purified *B. coagulans* bacteria are available from the American Type Culture Collection (Rockville, Md.) using the following accession numbers: *B. coagulans* Hammer NRS 727 (ATCC# 11014), *B. coagulans* Hammer strain C (ATCC# 11369), *B. coagulans* Hammer (ATCC# 31284), and *B. coagulans* Hammer NCA 4259 (ATCC# 15949). Purified *B. coagulans* bacteria are also available from the Deutsche Sammlung von Mikroorganismen und Zellkuturen GmbH (Braunschweig, Germany) using the following accession numbers: *B. coagulans* Hammer 1915 (DSM# 2356), *B. coagulans* Hammer 1915 (DSM# 2383, corresponds to ATCC# 11014), *B. coagulans* Hammer (DSM# 2384, corresponds to ATCC# 11369), and *B. coagulans* Hammer (DSM# 2385, corresponds to ATCC# 15949). *B. coagulans* bacteria can also be obtained from commercial suppliers such as Sabinsa Corporation (Piscataway, N.J.) or K.K. Fermentation, Kyoto, Japan.

These *B. coagulans* strains and their growth requirements have been described previously (Baker et al, *Can. J. Microbiol.* 6:557–563, 1960; Blumenstock, "*Bacillus coagulans* Hammer 1915 und andere thermophile oder mesophile, sauretolerante *Bacillus*-Arten-eine taxonomische Untersuchung", Doctoral thesis, Univ. Gottingen, 1984; Nakamura et al, *Int. J. Syst. Bacteriol.*, 38:63–73, 1988). Strains of *B. coagulans* can also be isolated from natural sources (e.g., heat-treated soil samples) using well known procedures (*Bergey's Manual of Systemic Bacteriology*, Vol. 2, p. 1117, Sneath, P. H. A. et al., eds., Williams & Wilkins, Baltimore, Md., 1986). The results described herein were obtained with *B. coagulans* Hammer obtained from the American Type Culture Collection (ATCC# 31284) which was grown as described herein and stored in lyophilized aliquots at −80° C. All *B. coagulans* that exhibit the properties described herein are considered equivalents of this strain.

*B. coagulans* had previously been mischaracterized as a *Lactobacillus* in view of the fact that as originally described, this bacterium was labeled as *Lactobacillus sporogenes* (See Nakamura et al, *Int. J. Syst. Bacteriol.*, 38:63–73, 1988). However, this was incorrect because *B. coagulans* produces spores and through metabolism excretes L(+)-lactic acid, both aspects which provide key features to its utility. Instead, these developmental and metabolic aspects required that the bacterium be classified as a lactic acid *bacillus*, and therefore it was renamed.

It is also not generally appreciated that classic *Lactobacillus* and/of *Bifidobacterium* species are unsuitable for colonization of the gut due to their instability in the harsh pH environment of the bile, particularly human bile. In contrast, the preferred *Bacillus* species are able to survive and colonize the gut in the bile environment.

2. Growth of *B. coagulans*

*B. coagulans* is aerobic and facultative, grown typically in nutrient broth, pH 5.7 to 6.8, containing up to 2% (by wt) NaCl, although neither NaCl nor KCl are required for growth. A pH of about 4 to about 7.5 is optimum for initiation of growth from spores. It is optimally grown at about 30° C. to about 45° C., and the spores can withstand pasteurization. It exhibits facultative and heterotrophic growth by utilizing a nitrate or sulphate source. Additional metabolic characteristics of *B. coagulans* are summarized in Table 1.

TABLE 1

| Characteristic | *B. coagulans* Response |
|---|---|
| Catalase production | Yes |
| Acid from D-Glucose | Yes |
| Acid from L-Arabinose | Variable |
| Acid from D-Xylose | Variable |
| Acid from D-Mannitol | Variable |
| Gas from Glucose | Yes |
| Hydrolysis of Casein | Variable |
| Hydrolysis of Gelatin | No |
| Hydrolysis of Starch | Yes |
| Utilization of Citrate | Variable |
| Utilization of Propionate | No |
| Degradation of Tyrosine | No |
| Degradation of Phenylalanine | No |
| Nitrate reduced to Nitrite | Variable |
| Allatoin or Urate Required | No |

*B. coagulans* can be grown in a variety of media, although it has been found that certain growth conditions produce a culture which yields a high level of sporulation. For example, sporulation is enhanced if the culture medium includes 10 milligrams per liter of manganese sulfate, yielding a ratio of spores to vegetative cells of about 80:20. In addition, certain growth conditions produce a bacterial spore which contains a spectrum of metabolic enzymes particularly suited for the present invention, i.e., production of lactic acid and enzymes for the enhanced probiotic activity and biodegradation. Although spores produced by these particular growth conditions are preferred, spores produced by any compatible growth conditions are suitable for producing a *B. coagulans* useful in the present invention.

Suitable media for growth of *B. coagulans* include Nutristart 701, PDB (potato dextrose broth), TSB (tryptic soy broth) and NB (nutrient broth), all well known and available from a variety of sources. Media supplements containing enzymatic digests of poultry and fish tissue, and containing food yeast are particularly preferred. A preferred supplement produces a media containing at least 60% protein, and about 20% complex carbohydrates and 6% lipids. Media can be obtained from a variety of commercial sources, notably DIFCO (Detroit, Mich.), Oxoid (Newark, N.J.), BBL (Cockeyesville, Md.), Advanced Microbial Systems, (Shakopee, Minn.), and Troy Biologicals (Troy, Mich.).

A preferred procedure for preparation of *B. coagulans* is described in the Examples.

B. Bifidogenic Oligosaccharides

Bifidogenic oligosaccharides, as used in the context of the present invention, are a class of sugars particularly useful for preferentially promoting the growth of a lactic acid bacteria of this invention. These oligosaccharides include fructo-oligosaccharides (FOS), gluco-oligosaccharides (GOS), other long-chain oligosaccharide polymers of fructose and/or glucose, and the trisaccharide raffinose, all of which are not readily digested by pathogenic bacteria. The preferential growth is promoted due to the nutrient requirements of this class of lactic acid bacterium as compared to pathogenic bacteria. Bifidogenic oligosaccharides are polymers that are utilized almost exclusively by the indigenous Bifidobacteria and *Lactobacillus* and can be similarly utilized by *Bacillus*. Deleterious microorganisms such as *Clostridium, Candida, Campylobacter, Klebsiella, Pseudomonas, Staphylococcus, Salmonella* and *E. Coli* cannot metabolize FOS or other bifidogenic oligosaccharides, and therefor use of these bifidogenic oligosaccharides in combination with a lactic acid bacteria of this invention, particularly *Bacillus*, allows the beneficial and probiotic bacteria to grow and to replace any undesirable or pathogenic microorganisms.

The use of bifidogenic oligosaccharides in compositions of the present invention provides a synergistic effect thereby increasing the effectiveness of the probiotic-containing compositions of this invention. This synergy is manifest at least by selectively increasing the ability of the probiotic bacterium to grow by increasing the food supplement for probiotic bacteria which preferentially selects for growth of the probiotic bacteria over many other bacterial species in the infected tissue. In addition, it is understood that Bifidobacteria and *Lactobacillus* are also producers of lactic acid. Bifidogenic oligosaccharides enable these probiotic organisms to proliferate preferentially over the undesirable bacteria that may be present in the tissue to be treated by the present invention, thereby furthering the probiotic state of the body. Thus, the presence of the bifidogenic oligosaccharides in the formulation allows for more effective inhibition of undesirable microbes by increasing the ability of all varieties of beneficial probiotic bacteria to grow and therefore provide benefit.

A preferred and exemplary bifidogenic oligosaccharide is FOS, although the other sugars can also be utilized, either alone or in combination.

FOS can be obtained from a variety of natural sources, including commercial suppliers. As a product isolated from natural sources, the components can vary widely and still provide the beneficial agent, namely FOS. FOS typically has a polymer chain length of from about 4 to 200 sugar units, with the longer lengths being preferred. For example, the degree of purity can vary widely so long as functional FOS is present in the formulation. Preferred FOS formulations contain at least 50% by weight of fructo-oligosaccharides compared to simple (mono or disaccharide) sugars such as glucose, fructose or sucrose, preferably at least 80% fructo-oligosaccharides, more preferably at least 90% and most preferably at least 95% fructo-oligosaccharides. Sugar content and composition can be determined by any of a variety of complex carbohydrate analytical detection methods as is well known.

Preferred sources of FOS include inulin, Frutafit IQ (tm) from Imperial Suiker Unie (Sugar Land, Tex.), NutraFlora (tm) from Americal Ingredients, Inc., (Anaheim, Calif.), Fabrchem, Inc., (Fairfield, Conn.), and Fruittrimfat Replacers and Sweeteners (Emeryville, Calif.). Bifidogenic oligosaccharides such as GOS, and other long chain oligosaccharides are also available from commercial vendors.

C. Cholesterol-Reducing Agents

1. Statins

Statins are a class of cholesterol-reducing agents, also known as HMG-CoA reductase inhibitors, which reduce cholesterol biosynthesis. These agents are competitive inhibitors of 3-hydroxy-3-methylglutaryl-co -enzyme-A-HMG-CoA reductase. Once administered to the body, statins are changed or "hydrolyzed" to an active beta-hydroxy -acid form which inhibits HMG-CoA reductase. This enzyme catalyzes the conversion of HMG-CoA to mevalonate, which is a critical, early and rate-limiting step in the biosynthesis of cholesterol. Once inhibited, cholesterol formation slows. The level of reduction in cholesterol is directly related to the amount of HMG-CoA reductase that is inhibited. Thus, cholesterol levels are directly related to enzyme inhibition, and enzyme inhibition is directly related to dosage of medication.

This relationship between cholesterol levels and dosage present risks of known serious side effects including liver and kidney damage. Statins are not tolerated well by many patients. Most patients are first given 10–20 mg per 70 kg adult per day. The dosage is gradually increased to up 80 mg per day as long as the patient's cardiologist doesn't see any increase in liver enzyme activity that may be caused by the medication. Severe liver complications have been reported in 3–5% of those that use statins. Other serious and potential fatal side effects have been reported as well. In addition, many medications are contradicted by statins and these contradictions also have the potential for fatality. The addition of a safe and effective amounts of a lactic acid bacteria of this invention, such as *B. coagulans*, to a composition enhances the action of statins which allows lower doses of statins to be used and reduces many of the side effects that are experienced at typical therapeutic levels.

Statins are well known and come in a variety of forms, and therefore the invention is not to be construed as so limited. Preferred statins include cerivastatin, fluvastatin, lovastatin, pravastatin, simvastatin, and the like, and can be obtained from a variety of commercial suppliers, such as under the trade names Baycor (Bayer), Lescol (Sandoz), Mevacor (Merck), Pravachol (Bristol-Meyers Squibb) or Zocor (Merck).

Fluvastatin has the chemical formula 7-[3-(4-fluorophenyl)-1-(1-methylethyl)-1H-indol-2-yl]-3,5-dihydroxy-6-heptenoic acid, monosodium salt. Fluvastatin sodium is a white to pale yellow, hygroscopic powder soluble in water, ethanol and methanol.

Simvastatin is derived synthetically from a fermentation product of *Aspergillus terreus*. After oral ingestion, simvastatin, which is an inactive lactone, is hydrolyzed to the corresponding beta-hydroxyacid form. Simvastatin has the chemical formula butanoic acid, 2,2-dimethyl-, 1,2,3,7,8,8a-hexahydro-3,7-dimethyl-8-[2-(tetrahydro-4-hydroxy-6-oxo-2H-pyran-2-yl)-ethyl]-1-naphthalenyl ester, (1S-[1alpha, 3alpha, 7beta, 8beta(2S*,4S*), −8abeta]]. The empirical formula of simvastatin is $C_{25}H_{3805}$ and its molecular weight is 418.57. Simvastatin is a white to off-white, nonhygroscopic, crystalline powder that is practically insoluble in water, and freely soluble in chloroform, methanol and ethanol.

2. Bile Sequestration Compounds

Cholesterol is the major, and probably the sole precursor of bile acids. During normal digestion, bile acids are secreted via the bile from the liver and gall bladder into the intestines. Bile acids emulsify the fat and lipid materials present in food, thus facilitating absorption. A major portion of the bile acids secreted is reabsorbed from the intestines and returned via the portal circulation to the liver, thus completing the enterohepatic cycle. Only very small amounts of bile acids are found in normal serum.

Compounds which bind bile acids in the intestine thereby prevent their reabsorption into the blood and recycling through the liver, and the complexes are excreted. Because the liver needs cholesterol to make bile, the liver increases its uptake of cholesterol from the blood, thereby reducing serum cholesterol.

However, bile sequestration agents can produce side effects which are controlled by the use of a lactic acid bacteria in combination. These side effects include black stools, stomach pain with vomiting or nausea, constipation, sudden weight loss, gastrointestinal indigestion, nausea and vomiting, stomach pain, bloating and the like conditions. A lactic acid bacteria is included and functions as an agent to alleviate constipation and improve overall digestive function.

Agents which reduce cholesterol by acting to sequester bile acids are a preferred cholesterol-reducing agent according to the present invention, and include colestipol and cholestyramine.

a. Colestipol

Colestipol, usually in the form of colestipol hydrochloride, binds bile acids in the intestine forming a complex that is excreted in the feces. This nonsystemic action results in a partial removal of the bile acids from the enterohepatic circulation, preventing their reabsorption. Since colestipol hydrochloride is an anion exchange resin, the chloride anions of the resin can be replaced by other anions, usually those with a greater affinity for the resin than chloride ion.

The increased fecal loss of bile acids due to colestipol hydrochloride administration leads to an increased oxidation of cholesterol to bile acids. This results in an increase in the number of low-density lipoprotein (LDL) receptors, increased hepatic uptake of LDL and a decrease in beta lipoprotein or low density lipoprotein serum levels, and a decrease in serum cholesterol levels.

Colestipol hydrochloride is a high molecular weight basic anion-exchange copolymer of diethylenetriamine and 1-chloro-2,3-epoxypropane, with approximately 1 out of 5 amine nitrogens protonated (chloride form). It is a light yellow water-insoluble resin which is hygroscopic and swells when suspended in water or aqueous fluids. Colestipol is also tasteless and odorless, and is typically formulated as granules using inactive carriers such as silicon dioxide.

Colestipol hydrochloride is hydrophilic, and because it is virtually water insoluble (99.75%) it is not hydrolyzed by digestive enzymes. The high molecular weight polymer in colestipol hydrochloride apparently is not absorbed. In humans, less than 0.17% of a single 14C-labeled colestipol hydrochloride dose is excreted in the urine when given following 60 days of chronic dosing of 20 grams of colestipol hydrochloride per day.

Colestipol is available from a variety of commercial suppliers, such as under the trade names Colestid (Upjohn), Colestipid, Cholestabyl and Lestid.

Thus, typical dosages of colestipid for use in the present invention comprise administration of a composition of this invention which comprises about 1 to 20 grams (gm), preferably about 4 to 15 gm, and more preferably about 6–8 gm per 70 kg adult per day, depending upon the patient's metabolism and tolerance, and the assessments of the physician.

b. Cholestyramine

Cholestyramine is a cholesterol lowering agent which is typically used in the form of the chloride salt of a basic anion exchange resin.

Cholestyramine resin adsorbs and combines with the bile acids in the intestine to form an insoluble complex which is excreted in the feces. This results in a partial removal of bile acids from the enterohepatic circulation by preventing their absorption.

The increased fecal loss of bile acids due to cholestyramine administration leads to an increased oxidation of cholesterol to bile acids, a decrease in beta lipoprotein or low density lipoprotein plasma levels and a decrease in serum cholesterol levels. Although in man, cholestyramine produces an increase in hepatic synthesis of cholesterol, plasma cholesterol levels fall.

Cholestyramine resin is quite hydrophilic, but insoluble in water, and is not absorbed from the digestive tract. Cholestyramine is available from a variety of commercial suppliers, for example under the trade names Questran (Bristol-Myers Squibb Company), Cuemid, Colestrol, Lismol and Quantalan.

3. Fibrin

The invention further contemplates the use of fiber products (ie., "fibrin") such as fibric acid derivatives as cholesterol-reducing agents. The action of these fiber products is to bind cholesterol in the form of free cholic acid and thereby remove them from bioavailability. An exemplary fibrin includes gemfibrozil (Lopid), fenofibrate (Tricor), psyllium, wheat bran, oat bran, rice bran, corn bran, konjak flour (glucomannan), Jerusalem artichoke flour, fruit fiber and any other functional food products containing these fiber products that have been demonstrated to aid in the reduction of serum lipids.

The combination of a subject fibrin with a lactic acid-producing bacteria of this invention into a therapeutic composition provides a more effective therapeutic by increasing the amount of bile acids that can be bound. This has been the missing element in fiber-based cholesterol products.

4. Other Agents

The invention further contemplates other agents which possess the capacity to reduce cholesterol, and are considered useful in a composition in combination with a lactic acid bacteria according to the present invention.

Nicotinic acid (niacin) is a preferred cholesterol-reducing agent. Niacin lowers total and LDL cholesterol and raises HDL cholesterol, and also lowers triglycerides. The dose of niacin required to lower cholesterol is about 100 times more than the Recommended Daily Allowance (RDA) for niacin and thus can potentially be toxic. Therefore, the drug must be taken under a doctor's care.

Also contemplated as a cholesterol-reducing agent is salicylic acid (aspirin). Aspirin has been shown to have a protective effect against heart attacks in patients with clogged blood vessels, and can also be used in a composition according to the present invention. The cholesterol-reducing mechanism is believed to be based on the acidic properties of aspirin, and as such the acid deconjugates the bile: cholesterol complex, reducing bioavailability.

D. Therapeutic Compositions

Compositions of this invention suitable for use in controlling or reducing cholesterol comprise a lactic acid-producing bacteria, preferably *B. coagulans, B. coagulans* spores, or combinations thereof, and an effective amount of a therapeutic agent selected from the group consisting of a cholesterol-reducing agent and a bifidogenic oligosaccharide in various formulations.

The active lactic acid-producing bacteria ingredient typically comprises about 0.1% to about 50% by weight of the final composition, preferably 1% to 10% by weight, in a formulation suitable for oral administration.

A typical therapeutic composition will contain in a one gram dosage formulation from $2 \times 10^5$ to $10^{10}$ colony forming units of viable lactic acid-producing bacteria or bacterial spore (in the case of *Bacillus coagulans*).

A typical therapeutic composition can contain one or more of the following active agents in addition to a lactic acid bacteria as described further herein: bifidogenic oligosaccharide and/or cholesterol reducing agent, in various combinations depending upon the specific formulation.

A preferred composition will include about 10 milligrams (mg) to one gram of bifidogenic oligosaccharide, preferably from 100 to 500 mg, per gram of composition.

As described herein, a therapeutic composition may also comprise about 1 to 80 mg of statin per gram of composition.

A therapeutic composition may also comprise about 0.1 to 0.8 gm of bile sequestering compound per gram of composition.

A therapeutic composition may also comprise about 10 mg to 0.5 gm of fibrin per gram of composition.

The formulation for a therapeutic composition of this invention may include other probiotic agents or nutrients for promoting growth.

Particularly preferred therapeutic compositions further contain cholic acid complexation agents which inhibit cholic acid re-adsorption and thereby increase excretion of cholic acid with the bile. Exemplary complexation agents include metal salts such as calcium, chromium, copper, iodine, iron, magnesium, manganese, potassium sodium, zinc and the like salts. Preferred salts are calcium, chromium, magnesium and potassium. For oral administration and adsorption, certain salt compounds are preferred, although not required. Particularly preferred salts are formed using citrate, gluconate and picollinate, as is well known. Preferred compounds are calcium citrate, potassium gluconate, magnesium citrate and chromium picollinate.

Cholic acid complexation agents are particularly preferred because they add beneficial aspect to the therapeutic invention. In particular, they increase the rate of excretion of cholic acid by forming complexes which are not re-adsorbed which in turn reduces the amount of cholesterol precursors available for cholesterol biosynthesis. Depletion of cholic acid by this pathway synergistically increases the effectiveness of the active agents by assisting in the primary goal of reducing cholesterol.

The compositions may also include known antioxidants, buffering agents, and other agents such as vitamins or minerals. The other agents in the compositions can also be either synergists or active agents, can be inactive, such as a carrier, or can be aesthetic, such as colorings or flavorings as described herein.

Preferred additional components of a therapeutic composition of this invention can include assorted colorings or flavorings well known in the art, vitamins, enzymes and other nutrients. Preferred vitamins include vitamins B, C, D, E, folic acid, K, niacin, and the like vitamins. Dietary or supplementary enzymes such as lactase, amylase, glucanase, catalase, and the like enzymes can also be included.

Exemplary vitamins are used in the composition as follows: choline (160 mg/lb), B-6 (10 mg/lb), B-12 (2 ug/lb), niacin (120 mg/lb), pantothenic acid (4 mg/lb), riboflavin (12 mg/lb), inositol (1 gm/lb), thiamine (1.5 mg/lb), folic acid (0.5 mg/lb), and the like.

Chemicals used in the present compositions can be obtained from a variety of commercial sources, including Spectrum Quality Products, Inc (Gardena, Calif.), Seltzer Chemicals, Inc., (Carlsbad, Calif.) and Jarchem Industries, Inc., (Newark, N.J.).

The active agents are combined with a carrier that is physiologically compatible with the gut tissue of a human or animal to which it is administered. That is, the carrier is preferably substantially inactive except for surfactant properties used in making a suspension of the active ingredients. The compositions may include other physiologically active constituents that do not interfere with the efficacy of the active agents in the composition.

A preferred therapeutic composition may also contain one or more of the following minerals: calcium citrate (15–350 mg), potassium gluconate (5–150 mg), magnesium citrate (5–15 mg) and chromium piccolinate (5–200 micrograms), with the amounts specified to be administered per day. The formulation may be completed in weight using any of a variety of carriers and/or binders.

Carriers can be solid-based dry materials for formulations in tablet, capsule or powdered form, and can be liquid or gel-based materials for formulations in liquid or gel forms, which forms depend, in part, upon the routes of administration.

Typical carriers for dry formulations include trehalose, malto-dextrin, rice flour, micro-crystalline cellulose (MCC) magnesium stearate, inositol, FOS, gluco-oligosaccharides (GOS), dextrose, sucrose, and the like carriers.

Suitable liquid or gel-based carriers are well known in the art, such as water and physiological salt solutions, urea, alcohols and glycols such as methanol, ethanol, propanol, butanol, ethylene glycol and propylene glycol, and the like. Preferably, water-based carriers are about neutral pH.

Suitable carriers include aqueous and oleaginous carries such as, for example, white petrolatum, isopropyl myristate, lanolin or lanolin alcohols, mineral oil, sorbitan monooleate, propylene glycol, cetylstearyl alcohol (together or in various combinations), hydroxypropyl cellulose (MW=100,000 to 1,000,000), detergents (e.g., polyoxyl stearate or sodium lauryl sulfate) and mixed with water to form a lotion, gel, cream or semi-solid composition. Other suitable carriers comprise water-in-oil or oil-in-water emulsions and mixtures of emulsifiers and emollients with solvents such as sucrose stearate, sucrose cocoate, sucrose distearate, mineral oil, propylene glycol, 2-ethyl-1,3-hexanediol, polyoxypropylene-15-stearyl ether and water. For example, emulsions containing water, glycerol stearate, glycerin, mineral oil, synthetic spermaceti, cetyl alcohol, butylparaben, propylparaben and methylparaben are commercially available. Preservatives may also be included in the carrier including methylparaben, propylparaben, benzyl alcohol and ethylene diamine tetraacetate salts. Well-known flavorings and/or colorants may also be included in the carrier. The composition may also include a plasticizer such as glycerol or polyethylene glycol (MW=800 to 20,000). The composition of the carrier can be varied so long as it does not interfere significantly with the pharmacological activity of the active ingredients or the viability of a lactic acid bacteria included in the composition.

A typical composition of this invention can further contain any of the following inactive ingredients: acacia, aspartame, citric acid, D&C Yellow No. 10, FD&C Yellow No. 6, flavor (natural and/or artificial), polysorbate 80, propylene glycol alginate, colloidal silicon dioxide and sucrose and xanthan gum.

A composition can also contains the following inactive ingredients: aspartame, beta carotene, citric acid, flavor (natural and artificial), glycerine, maltol, mannitol, and methylcellulose.

Exemplary and preferred formulations are described in the Examples. Particularly preferred formulations for a therapeutic composition of this invention are described in the Examples.

E. Therapeutic Methods for Reducing Cholesterol

The present invention contemplates a method for decreasing serum LDL cholesterol and triglycerides, and increasing serum HDL cholesterol. The method comprises administration of a therapeutic composition of this invention containing the active ingredients to a human or animal in various dosage regimens as described herein to achieve the therapeutic result.

Administration of a therapeutic composition is preferably to the gut using a gel, suspension, aerosol spray, capsule, tablet, powder or semi-solid formulation (e.g., a suppository) containing a therapeutic composition of this invention, all formulated using methods well known in the art. Administration of the compositions containing the active ingredients effective in controlling or reducing cholesterol generally consist of one to ten unit dosages of 10 mg to 10 g per dosage of the composition for one day up to one month. Unit dosages are generally given once every twelve hours and up to once every four hours. Preferably two to four dosages of the composition per day, each comprising about 0.1 g to 5 g per dosage, for one to seven days are sufficient to control or reduce cholesterol.

A preferred method involves the administration into the digestive tract of from $10^4$ to $10^{12}$ viable bacterium or spore per day, preferably about from $10^7$ to $10^{10}$ viable bacterium or spores per day, and more preferably about from $5 \times 10^8$ to $10^9$ viable bacterium or spore per day.

The method further includes administration of one or more of the therapeutic agents described herein and selected from the group consisting of a bifidogenic oligosaccharide and a cholesterol reducing agent.

A preferred method comprises administering into the digestive tract from 10 mgs to 20 gms of fructo-oligosaccharide per day, preferably about 50 mg–10 gm, and more preferably about from 150 mgs to 5 gms of fructo-oligosaccharide per day.

Insofar as the invention can also contemplates administering a cholesterol reducing agent in a therapeutic composition, a composition administered according to the present invention may also contain one or more of the therapeutic agents described herein.

Thus, a composition may contain a statin as described herein for administration in the therapeutic method. Typical dosages of statins for use in the present method comprise administration of a composition of this invention in an amount of about 10 to 80 milligrams (mg), preferably about 40 to 80 mg per 70 kg adult per day, depending upon the patient's metabolism and tolerance, and the assessments of the physician.

A composition may contain a bile sequestering compound as described herein for administration in the therapeutic method. Thus, typical dosages of a bile sequestering compound for use in the present method comprise administration of a composition of this invention in an amount of about 1 to 20 grams (gm), preferably about 4 to 15 gm, and more preferably about 6–8 gm per 70 kg adult per day, depending upon the patient's metabolism and tolerance, and the assessments of the physician.

A fibrin can be used in a variety of dosage formulations, and therefore the invention is not to be construed as so limited. Typical dosages comprise administering to the digestive track from about 0.5 to 50 grams of fibrin per 70 kg adult per day, preferably about 5–10 gms per day.

Typical dosages of aspirin comprise administering from about 300 mg to 4 gms salicylic acid per 70 kg adult per day, preferably about 0.6 to 1.8 gms per day.

The method is typically practiced on any person at risk for conditions of elevated serum LDL cholesterol. These conditions include, but are not limited to, atherosclerosis, arterial sclerosis, myocardial infarction, heart attack, diabetes, coronary heart disease, angina pectoris or unstable angina.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The examples of embodiments are for illustration only.

F. Therapeutic Systems for Reducing Cholesterol

The invention further contemplates a therapeutic system for reducing serum cholesterol comprising a container comprising label and a therapeutic composition according to the present invention, wherein said label comprises instructions for use of the composition for reduction of serum cholesterol.

Typically, the system is present in the form of a package containing a therapeutic composition of this invention, or in combination with packaging material. The packaging material includes a label or instructions for use of the components of the package. The instructions indicate the contemplated use of the package component as described herein for the methods or compositions of the invention.

For example, a system can comprise one or more unit dosages of a therapeutic composition according to the invention. Alternatively, the system can contain bulk quantities of a therapeutic composition. The label contains instructions for using the therapeutic composition in either unit dose or in bulk forms as appropriate, and may include information regarding storage of the composition, disease indications, dosages, routes of administration and the like information.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Formulation of Therapeutic Composition

Formulation 1

| | | |
|---|---|---|
| B. coagulans | 500,000,000 | spores (~35 mg) |
| calcium citrate | 35 | milligrams (mg) |
| potassium gluconate | 10 | mg |
| magnesium citrate | 10 | mg |
| chromium piccolinate | 50 | micrograms (ug) |
| fructo-oligosaccharides | 200 | mg |
| micro-crystalline cellulose | 660 | mg |

Formulation 2

| | | |
|---|---|---|
| B. coagulans | 500,000,000 | spores (~35 mg) |
| calcium citrate | 35 | milligrams (mg) |
| potassium gluconate | 10 | mg |
| chromium piccolinate | 50 | micrograms (ug) |
| micro-crystalline cellulose | 870 | mg |

Formulation 3

| | | |
|---|---|---|
| B. coagulans | 500,000,000 | spores (~35 mg) |
| calcium citrate | 35 | milligrams (mg) |
| potassium gluconate | 10 | mg |
| magnesium citrate | 10 | mg |
| chromium piccolinate | 50 | micrograms (ug) |
| fructo-oligosaccharides | 500 | mg |
| micro-crystalline cellulose | 360 | mg |

Formulation 4

| | | |
|---|---|---|
| B. coagulans | 500,000,000 | spores (~35 mg) |
| calcium citrate | 35 | milligrams (mg) |
| potassium gluconate | 10 | mg |
| magnesium citrate | 35 | mg |
| chromium piccolinate | 50 | micrograms (ug) |
| fructo-oligosaccharides | 300 | mg |
| micro-crystalline cellulose | 535 | mg |

Formulation 5

| | | |
|---|---|---|
| B. coagulans | 1 billion | spores (~70 mg) |
| potassium gluconate | 10 | mg |
| magnesium citrate | 10 | mg |
| colestipol | 20 | mg |
| micro-crystalline cellulose | 890 | mg |

Formulation 6

| | | |
|---|---|---|
| B. coagulans | 1 billion | spores (~70 mg) |
| potassium gluconate | 10 | mg |
| magnesium citrate | 10 | mg |
| fructo-oligosaccharides | 300 | mg |
| colestipol | 40 | gm |
| micro-crystalline cellulose | 570 | mg |

Formulation 7

| | | |
|---|---|---|
| B. coagulans | 1 billion | spores (~70 mg) |
| potassium gluconate | 10 | mg |
| magnesium citrate | 10 | mg |
| simvastatin | 20 | mg |
| micro-crystalline cellulose | 890 | mg |

Formulation 8

| | | |
|---|---|---|
| B. coagulans | 1 billion | spores (~70 mg) |
| potassium gluconate | 10 | mg |
| magnesium citrate | 10 | mg |
| fructo-oligosaccharides | 300 | mg |
| simvastatin | 40 | mg |
| micro-crystalline cellulose | 570 | mg |

2. Preparation of B. coagulans Spores

A culture of dried *B. coagulans* spores was prepared as follows. Ten million spores were inoculated into a one liter culture containing 24 gms potato dextrose broth, 10 gms of enzymic digest of poultry and fish tissue, 5 gms of FOS and 10 gms MnSO4. The culture was maintained for 72 hours under a high oxygen environment at 37 degrees Centigrade to produce culture having about 150 billion cells per gram of culture. Thereafter, the culture was filtered to remove culture medium liquid, and the bacterial pellet was resuspended in water and freeze-dried. The freeze-dried powder is then ground to a fine powder using standard good manufacturing practice (GMP). The powder is then combined into Formulation 4 as described in Example 1 and placed into capsules in the amount of 0.5 gms per capsule.

3. Effect of *B. coagulans* Composition on Serum LDL

Controlled studies using 20 patients was conducted in which two tablets produced as in Example 2 were taken daily for 60 days, and the patients were monitored for LDL, HDL and serum triglycerides. The patients showed an average reduction of LDL cholesterol by 31–43%, an average increase of HDL cholesterol by 7–15%, and a decrease of serum triglyceride levels by 11–16%. During the treatment, 3 patients diagnosed with greater than 85% carotid artery blockage experienced a reduction in blockage to about 40% blockage. Although these 3 patients were all scheduled for shunt surgery based on the level of blockage, the surgeries were all canceled by their physicians after the treatment because the danger of diminished circulation had subsided.

In a related study, patients receiving about 150–500 million bacterial cells per day in combination with 500 mg FOS per day demonstrated a reduction of LDL cholesterol of about 30–40% after two weeks of daily administration.

The invention has been described in the above examples using a variety of formulations, although it should be apparent that various other carrier agents that are compatible with the probiotic compositions may be substituted in the examples to give similar results. Accordingly, the invention may be embodied in other specific forms without departing from it in spirit. The examples are to be considered in all respects only as illustrative and not as restrictive, and the scope of the invention is indicated by the claims that follow. All modifications which come within the meaning and range of the lawful equivalency of the claims are to be embraced within their scope.

What is claimed is:

1. A method for decreasing serum cholesterol, decreasing serum triglycerides, and increasing serum HDL in a patient comprising administering to said patient an effective amount of a composition comprising viable *Bacillus coagulans* bacteria.

2. The method of claim 1, wherein said *Bacillus coagulans* bacteria are *Bacillus coagulans* subspecies Hammer.

3. The method of claim 1, wherein said *Bacillus coagulans* bacteria are *Bacillus coagulans* subspecies Hammer deposited under ATCC deposit number 31284.

4. The method of claim 1, wherein said composition contains $2 \times 10^5$ to $1 \times 10^{10}$ viable bacteria per gram of composition.

5. The method of claim 1, wherein said composition contains $1 \times 10^7$ to $1 \times 10^{10}$ viable bacteria per gram of composition.

6. The method of claim 1, wherein said administering comprises introducing into the digestive tract from $10^8$ to $10^{10}$ viable bacteria per day.

7. The method of claim 1, wherein said composition contains $5 \times 10^8$ to $1 \times 10^9$ viable bacteria per gram of composition.

8. The method of claim 1 wherein said administering comprises introducing into the digestive tract from $5 \times 10^8$ to $5 \times 10^9$ viable bacteria per day.

9. The method of claim 1, wherein said administering comprises oral ingestion of said composition.

10. The method of claim 1, wherein said administering comprises introducing into the digestive tract from 0.1 to 5 grams per day of said composition.

11. The method of claim 1, wherein composition is in the form of a capsule, tablet, powder, semi-solid formulation, liquid, gel, suspension, or aerosol spray.

12. The method of claim 1, wherein said composition further comprises a cholesterol-reducing agent.

13. The method of claim 1, wherein said cholesterol-reducing agent is selected from the group consisting of a statin, a bile sequestering compound, a fiber product capable of binding cholesterol, niacin and aspirin.

14. The method of claim 13, wherein said statin is selected from the group consisting of cerivastatin, fluvastatin, lovastatin, pravastatin and simvastatin.

15. The method of claim 14, wherein said administering comprises introducing into the digestive tract from 10 to 80 milligrams of statin per day.

16. The method of claim 13, wherein said bile sequestering compound is selected from the group consisting of colestipol and cholestyramine.

17. The method of claim 16, wherein said administering comprises introducing into the digestive tract from 1 to 20 grams of bile sequestering compound per day.

18. The method of claim 16, wherein said administering comprises introducing into the digestive tract from 6 to 8 grams of bile sequestering compound per day.

19. The method of claim 13, wherein said fiber product is selected from the group consisting of gemfibrozil, fenofibrate, psyllium, bran, glucomannan and Jerusalem artichoke flour.

20. The method of claim 19, wherein said administering comprises introducing into the digestive tract from 500 milligrams to 50 grams of fiber per day.

21. The method of claim 1, wherein said composition further comprises a cholic acid complexation agent.

22. The method of claim 21, wherein said complexation agent is a salt of a metal selected from the group consisting of calcium, chromium, copper, iodine, iron, magnesium, manganese, potassium sodium, and zinc.

23. The method of claim 22, wherein said metal salt is provided in the form of calcium citrate, potassium gluconate, magnesium citrate or chromium picollinate.

24. The method of claim 1, wherein said composition further comprises a food substance, flavoring, vitamin or mineral.

25. The method of claim 24, wherein said vitamin is selected from the group consisting of choline, B-6, B-12, niacin, pantothenic acid, riboflavin, inositol, thiamine, and folic acid.

26. The method of claim 1, wherein said patient is at risk for atherosclerosis, arterial sclerosis, myocardial infarction, heart attack, diabetes, coronary heart disease, angina pectoris or unstable angina.

27. A method for decreasing serum cholesterol, decreasing serum triglycerides, and increasing serum HDL in a patient comprising administering to the digestive tract of said patient an effective amount of a composition comprising viable *Sporolactobacillus* P44 bacteria.

* * * * *

UNITED STATES PATENT AND TRADEMARK OFFICE
CERTIFICATE OF CORRECTION

PATENT NO. : 7,232,571 B2 Page 1 of 1
APPLICATION NO. : 10/978726
DATED : June 19, 2007
INVENTOR(S) : Farmer et al.

It is certified that error appears in the above-identified patent and that said Letters Patent is hereby corrected as shown below:

Title Page, Item (75), first line, "Scan Farmer, La Jolla, CA (US);" should read --Sean Farmer, La Jolla, CA (US);--.

Signed and Sealed this

Seventh Day of August, 2007

JON W. DUDAS
*Director of the United States Patent and Trademark Office*